United States Patent
Sullivan et al.

(10) Patent No.: US 7,725,180 B2
(45) Date of Patent: May 25, 2010

(54) METHOD AND APPARATUS FOR TESTING AN ALTERNATING CURRENT POWER SOURCE FOR DEFIBRILLATION COMPATIBILITY

(75) Inventors: Joseph L. Sullivan, Kirkland, WA (US); Richard C. Nova, Kirkland, WA (US)

(73) Assignee: Physio-Control, Inc., Redmond, WA (US)

( * ) Notice: Subject to any disclaimer, the term of this patent is extended or adjusted under 35 U.S.C. 154(b) by 1102 days.

(21) Appl. No.: 10/998,911

(22) Filed: Nov. 29, 2004

(65) Prior Publication Data

US 2006/0116726 A1 Jun. 1, 2006

(51) Int. Cl.
*A61N 1/00* (2006.01)
(52) U.S. Cl. .......................................................... 607/5
(58) Field of Classification Search .................. 607/5–8; 363/134
See application file for complete search history.

(56) References Cited

U.S. PATENT DOCUMENTS

| | | | | |
|---|---|---|---|---|
| 3,747,605 A | * | 7/1973 | Cook | 607/8 |
| 3,775,658 A | * | 11/1973 | Miles | 607/5 |
| 4,077,413 A | | 3/1978 | Partridge | |
| 4,233,659 A | * | 11/1980 | Pirkle | 363/134 |
| 4,328,808 A | * | 5/1982 | Charbonnier et al. | 607/8 |
| 5,285,779 A | * | 2/1994 | Cameron et al. | 607/5 |
| 5,575,807 A | | 11/1996 | Faller | |
| 6,038,473 A | | 3/2000 | Olson et al. | |
| 6,223,077 B1 | | 4/2001 | Schweizer et al. | |
| 6,289,243 B1 | | 9/2001 | Lin et al. | |
| 6,493,580 B1 | | 12/2002 | Cansell et al. | |
| 2002/0077666 A1 | | 6/2002 | Sherman | |
| 2004/0143297 A1 | | 7/2004 | Ramsey, III | |

FOREIGN PATENT DOCUMENTS

GB 1143141 2/1969

OTHER PUBLICATIONS

U.S. Patent Application entitled "Portable Defibrillator with Bypass Line Power Emergency Charging of Capacitor", U.S. Appl. No. 10/608,239, filed Jun. 27, 2003.
International Search Report for Patent Application No. PCT/US2004/007462, filing date: Mar. 11, 2004.

* cited by examiner

*Primary Examiner*—George Manuel
(74) *Attorney, Agent, or Firm*—Shumaker & Sieffert, P.A.

(57) ABSTRACT

A device tests a circuit that is a source of alternating current by measuring at least one electrical parameter of the circuit to determine whether the circuit is able to provide adequate energy for defibrillation by an external defibrillator. The device may test the circuit by applying a load to the circuit, and measuring one or more electrical parameters when the load is applied to the circuit. The device may be the external defibrillator itself, or a separate testing device. In some embodiments in which an external defibrillator tests a circuit, the defibrillator modifies a value of at least one therapy delivery parameter for a subsequent delivery of one or more defibrillation pulses based on the measured electrical parameter value measured. By modifying a therapy delivery parameter, the defibrillator may deliver defibrillation pulses at an energy level that is supportable by the circuit.

35 Claims, 11 Drawing Sheets

METHOD AND APPARATUS FOR TESTING AN ALTERNATING CURRENT POWER SOURCE FOR DEFIBRILLATION COMPATIBILITY

TECHNICAL FIELD

The invention relates to external defibrillators and, more particularly, to external defibrillators that use an alternating current power source for defibrillation of a patient.

BACKGROUND

Early external defibrillators delivered alternating current from a mains circuit, e.g., a building alternating current (ac) power circuit, to a patient. These early defibrillators delivered the a long burst, e.g., one or two seconds, of current at the mains voltage, e.g., 120 volts in the United States. Because these early defibrillators relied on the presence of a mains circuit receptacle for power, they were not portable, and could not reach many patients that required defibrillation.

These early defibrillators were eventually replaced by the type of defibrillator that is currently commercially available, i.e., external defibrillators use a direct current (dc) power source, e.g., a battery, as the source of energy for defibrillation of a patient. The dc power sources used by commercially available defibrillators allow them to be self-contained and completely portable. Some commercially available defibrillators may be plugged into a receptacle to receive alternating current from a building circuit, but merely use the current to recharge the dc power source.

Commercially available external defibrillators typically include one or more capacitive elements that store a charge from the dc power source, which is then delivered to the patient in the form of a defibrillation pulse. These defibrillators may also include switches or other wave-shaping circuits in order to deliver the exponentially decaying monophasic pulse output by the capacitive elements as a truncated exponentially decaying monophasic, biphasic, or multiphasic pulse. The defibrillation pulses delivered by commercially available defibrillators have a significantly higher voltage and are significantly shorter than the mains voltage bursts delivered by the early defibrillators and, for that reason, are considered to be more therapeutically effective than the mains voltage bursts delivered by the early defibrillators.

However, because these commercially available external defibrillators include a battery, capacitive elements, and charging circuitry to quickly charge the capacitive elements to a high voltage from the battery, they may be significantly heavy and expensive. Further, defibrillators, such as automated external defibrillators (AEDs), are increasingly being provided at locations, such as homes and small offices, where having a self-contained power source for the sake of portability is not a necessity. Consequently, for such locations, it may be desirable to provide a defibrillator that is not self-contained, but which provides high voltage defibrillation pulses with similar efficacy to those provided by commercially external defibrillators, and may be lighter and less expensive than commercially available defibrillators.

U.S. Published Patent Application No. 2004/0143297 by Ramsey III describes a defibrillator that does not require a battery. Instead, the defibrillator described by Ramsey III charges an array of capacitors directly from a mains circuit, and delivers the energy stored by the capacitors to a patient as a defibrillation in much the same manner as commercially available defibrillators. The defibrillator described by Ramsey III charges the capacitors in parallel, then discharges the capacitors in series to provide a voltage that is significantly higher than that mains voltage for the defibrillation pulses.

Because the defibrillator described by Ramsey III would not include a battery, it might be lighter and less expensive than commercially available defibrillators. However, because the defibrillator described by Ramsey III requires several high value capacitors in order to achieve the high voltage desired for efficacious defibrillation, it would likely be more expensive than a defibrillator that delivered energy directly from a mains circuit to a patient, like the early defibrillators. Consequently, a defibrillator that delivers energy directly from a mains circuit to a patient, like the early defibrillators, but does so in the form of high voltage "pulses" with a desired efficacy, like commercially available defibrillators, might provide the most desirable option in terms of weight and cost for location and applications that do not require mobility.

However, even assuming that such a defibrillator were to become available, its use may be limited by the inability of ac mains circuits in homes, offices and other buildings to deliver adequate energy, e.g., power, voltage, current or charge, for defibrillation. For example, typically a peak current of approximately 10 amps to approximately 20 amps is required to be delivered to a patient for defibrillation. Patient impedances generally fall within the range from approximately 25 ohms to approximately 150 ohms, resulting in a peak power required for defibrillation of a patient that is within a range from approximately 2500 watts to 60,000 watts. Therefore, the peak current draw from a 120 volt ac mains circuit would be within a range from approximately 20 amps to approximately 500 amps.

The resistance of an ac mains circuit in a building may be too high to reliably provide peak current throughout this range. For example, according to the well-known relationship between voltage, current and resistance, a 120 volt ac mains circuit with a resistance of 1 ohm will only be capable of providing an instantaneous current of 120 amps. In some cases, a resistance of as little as 0.1 ohm may render a circuit unable to support delivery of defibrillation pulses to a particular patient, with a particular patient resistance, at a specified energy level.

The resistance of a building circuit may be too high to support defibrillation due to, for example, improper wiring or degradation of materials over time. Further, the fact that a circuit is unable to provide adequate energy for defibrillation, or at least unable do so reliably and for a full range of defibrillation pulse energy levels, will likely not be apparent to the purchaser, installer, or user of a defibrillator that is coupled to that circuit. Nonetheless, because defibrillators are critical, life-saving devices, it is imperative that they be capable of reliably delivering defibrillation pulses at any desired energy level.

SUMMARY

In general, the invention is directed to devices and associated techniques for determining whether a circuit that is a source of alternating current, e.g., an alternating current (ac) mains circuit, is able to provide adequate energy; e.g., power, voltage, current or charge, to support defibrillation. In particular, the invention provides a device that tests an ac circuit for compatibility with a defibrillator that delivers energy from the ac circuit to the patient in the form of a defibrillation pulse. The device may be the defibrillator itself, or a separate testing device. In either case, the device allows one to determine whether the circuit is able to support defibrillation by such a defibrillator and, importantly, to make this determination before the defibrillator is needed to treat a patient.

The ac circuit may include a receptacle, and the defibrillator may include a plug to receive energy in the form of alternating current at the mains voltage from the receptacle. The defibrillator delivers the energy from the circuit to a patient in the form of a defibrillation pulse that is a fraction of a cycle of the alternating current sinusoid provided by circuit, or one or more cycles of the alternating current sinusoid. Because each of the defibrillation pulses delivered by the defibrillator comprises a portion of the ac sinusoid provided by the circuit, they may be referred to as "ac defibrillation pulses." Also, the defibrillator does not include a battery, capacitors, or other energy storage elements to store the energy received from the circuit prior to delivering the energy to a patient as a defibrillation pulse. Consequently, the delivery of energy from the circuit to a patient by the defibrillator may be said to be "direct," in the sense that the energy is not stored for a significant amount of time prior to delivery to the patient.

The defibrillator may include a transformer that delivers the defibrillation pulse to a patient at a stepped up voltage relative to the voltage of the alternating current received from ac circuit, which may be a more therapeutically desirable voltage than the ac mains voltage. Further, the defibrillator may include a switching module that controls the coupling of the transformer to the ac circuit, i.e., controls the duration of the delivered defibrillation pulses by truncating the sinusoidal ac waveform provided by the circuit. In this manner, the switching module may control the fraction or number of cycles of alternating current at the stepped up voltage delivered to the patient.

The device may test the circuit by measuring one or more electrical parameters, such as voltage or current. In such embodiments, the device includes a measurement module to measure the electrical parameter, and an analysis module to determine whether the circuit supports defibrillation by the defibrillator based on the electrical parameter value measured by the measurement module. In some embodiments, the device may measure an electrical parameter across a load when the load is applied to the circuit. For example, the measurement module may include a voltmeter to measure the voltage across the load when it is applied to the circuit.

In some embodiments, the analysis module includes analog circuitry to compare a signal output by the measurement module to indicate the measured value to a threshold, and thereby determine whether the circuit is capable of providing adequate energy for defibrillation. In such embodiments, the analog circuitry may output a signal that drives a light or audible alarm. In this manner, the analysis module may indicate to a user whether the circuit is capable of providing adequate energy for defibrillation. In other embodiments, the analysis module may include processor that compares the measured value to a threshold value stored in a memory, and controls a user interface that may include a light or an audible alarm to provide an indication to a user.

In some embodiments in which the analysis module includes an processor, the processor may further process the measured electrical parameter value in order to determine whether the circuit is capable of providing adequate energy for defibrillation. For example, the processor may determine whether the circuit supports defibrillation based on the measured voltage by determining the amount of current drawn by the circuit based on the measured voltage and the known resistance of a load. The processor may compare the determined current value to a threshold value stored in memory, such as 400 amps, and determine whether the circuit supports defibrillation based on the comparison.

In other embodiments, in addition to measuring voltage across a load when the load is applied to the circuit, the measurement module measures the open circuit voltage of the circuit when the load has not been applied. In such embodiments, the processor may determine the resistance of the circuit based on the measured voltages and the known resistance of the load, and may determine whether the circuit can support defibrillation by comparing the resistance to a threshold value, such as 0.1 ohm. Devices that determine the compatibility of a circuit based on its resistance may require a smaller load than some devices that determine circuit compatibility based on the current output by the circuit during application of the load, in which the load must be large enough to draw current similar to that drawn during a defibrillation pulse. A smaller load may reduce the size and cost of a device used to test circuit compatibility.

In some embodiments in which the device that tests the circuit is the defibrillator itself, the defibrillator applies a load to the circuit by directly coupling the load to the circuit. In other embodiments, the defibrillator couples the load to its therapy delivery module. In such embodiments, the therapy delivery module delivers a defibrillation pulse to the load, and the measurement module measures the electrical parameter when the defibrillation pulse is delivered to the load. For example, the measurement module may include an ac voltmeter that measures a voltage across the load when the defibrillation pulse is delivered to the load. In such embodiments, the defibrillator determines whether the circuit is capable of providing adequate energy to support defibrillation by determining whether therapy delivery module was able to deliver the defibrillation pulse at an adequate energy level. In some embodiments, the load may be a patient.

Whether the device that tests the circuit is the defibrillator or a separate device, the device provides an indication to a user as to whether the circuit is compatible with defibrillation. For example, the device may provide the indication visually via, for example, one or more lights or a display. In some embodiments, the device may additionally or alternatively indicate compatibility audibly via a speaker. Further, in some embodiments, the device may include a data interface, and communicate the determination of compatibility to another device via the data interface. For example, the device may include a network interface, and communicate the determination of whether the circuit is compatible to a remote computing device, such as a computer of a remote monitoring or alarm system, via a network.

The device may test the circuit automatically upon being plugged into a receptacle of the circuit, or upon receiving a request from a user via a user interface. In embodiments in which the device is plugged into the receptacle of the circuit for a longer period of time, the device may test the circuit periodically. In this manner, the device may monitor a circuit over time to detect whether a circuit that was previously determined to be able to support defibrillation continues to be able to support defibrillation.

In some embodiments, a defibrillator modifies a value of at least one therapy delivery parameter for a subsequent delivery of one or more defibrillation pulses based on the ability of the circuit to provide adequate energy to support defibrillation. In particular, the defibrillator may modify therapy delivery parameters based on one or more electrical parameter values measured when a load is applied to the circuit, e.g., applied directly to the circuit or applied to the therapy delivery circuit of the defibrillator as described above. For example, the defibrillator may modify therapy delivery parameters based on a voltage measured across the load when applied to the circuit, the current output by the circuit when the load was applied, or the resistance of the circuit determined as described above. By modifying one or more therapy delivery parameters, the defibrillator may deliver defibrillation pulses at an energy level that is supported by the circuit.

In some embodiments, during actual use with a patient, the defibrillator may also measure the resistance of the patient, and may adjust the one or more therapy delivery parameters based on both the value of the electrical parameter measured when the load is applied to the circuit and the patient resistance. The amount of current drawn from the circuit by the transformer during delivery of a defibrillation pulse is inversely related to patient resistance. Consequently, while the circuit may support delivery of a defibrillation pulse at a first voltage for a first patient, the circuit may not be able to support delivery of a defibrillation pulse at the first voltage for a second patient with a lower resistance than the first patient. By modifying the therapy delivery parameters based on both the measured value of the electrical parameter and the resistance of the patient, the defibrillator may be able to deliver defibrillation pulses at an energy level that is supported by the circuit across a range of patient resistances.

The defibrillator may, for example, modify the turns ratio of the transformer used to step up the voltage of the alternating current provided by circuit to a suitable level for defibrillation, e.g., with one or more switches. By modifying the turns ratio of the transformer, the defibrillator may adjust the amount of current drawn by the transformer to a level supported by the circuit in light of patient resistance. In some embodiments, the defibrillator may additionally modify the programmed duration of defibrillation pulses, e.g., the number of cycles of alternating current delivered to the patient during the defibrillation pulse, so that the amount of energy delivered to the patient remains substantially the same after modification of the turns ratio, i.e., modification of the amount of current delivered to the patient.

In some embodiments, the load that the defibrillator applies to the circuit is the patient. In such embodiments, the defibrillator may measure one or more electrical parameters during delivery of a first defibrillation pulse to the patient. The defibrillator may then modify one or more therapy delivery parameters for delivery of a subsequent pulse at an energy level supported by the circuit in light of the patient resistance.

In one embodiment, the invention is directed to a device comprising a measurement module, and an analysis module. The measurement module measures a value of at least one electrical parameter of a circuit that is a source of alternating current, and the analysis module determines whether the circuit is able to provide adequate energy for defibrillation based on the measured electrical parameter value.

In another embodiment, the invention is directed to a method comprising measuring a value of at least one electrical parameter of a circuit that is a source of alternating current, and determining whether the circuit is able to provide adequate energy for defibrillation based on the measured electrical parameter value.

In another embodiment, the invention is directed to an external defibrillator that includes a therapy delivery module that is coupled to a circuit that is a source of alternating current. The external defibrillator also includes a measurement module to measure a value of at least one electrical parameter of the circuit, and a processor. The processor modifies a value of at least one therapy delivery parameter based on the measured electrical parameter value, and controls the therapy delivery module to deliver energy from the circuit to the patient as a defibrillation pulse according to the modified therapy delivery parameter value.

In another embodiment, the invention is directed to a method that comprises measuring a value of at least one electrical parameter of circuit that is a source of alternating current, modifying a value of at least one therapy delivery parameter based on the measured electrical parameter value, and delivering energy from the circuit to the patient as a defibrillation pulse according to the modified therapy delivery parameter value.

In another embodiment, the invention is directed to a computer-readable medium comprising instructions. The instructions cause a programmable processor to control measurement of a value of at least one electrical parameter of a circuit that is a source of alternating current, modify a value of at least one therapy delivery parameter based on the measured electrical parameter value, and control the therapy delivery module to deliver energy from the circuit to the patient as a defibrillation pulse according to the modified therapy delivery parameter value.

The invention may provide a number of advantages. For example, a device according to the invention may allow an installer of a defibrillator that delivers energy from an ac circuit to a patient in the form of defibrillation pulses to identify a compatible circuit within a desired installation location, such as a home or other building. In this manner, the invention may overcome the potential unreliability of such defibrillators that is a result of variations in the amount of energy available such circuits, and may thereby enable the development and use of such defibrillators. If no circuit within a location is compatible, a battery-powered defibrillator of the type that is currently commercially may be selected for the location.

The device may also monitor a circuit initially determined to be compatible with defibrillation over time. The resistance of a circuit may increase over time due to degradation of materials. The device may be able to identify when the resistance of the circuit has increased such that the circuit no longer supports defibrillation, and alert a user that the circuit no longer supports defibrillation. In response to the alert, the user can identify a different circuit within the location that will support defibrillation, or select a battery-powered defibrillator for the location.

In some situations, a defibrillator that delivers energy from an ac circuit to a patient in the form of defibrillation pulses will nonetheless be plugged into a circuit that is unable to reliably provide fully adequate energy for defibrillation. For example, a user may ignore an alert indicating that the circuit does not support defibrillation, the circuit may have very recently or suddenly become unable to support defibrillation, or the defibrillator may be plugged into a receptacle of the circuit just prior to being used to treat a patient. In such situations, a defibrillator according to the invention delivers defibrillation pulses at an energy level supported by the circuit and, in some embodiments, in light of the patient resistance. Delivering defibrillation pulses at a current level supported by the circuit is preferable to not delivering defibrillation pulses to a patient in cardiac arrest.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
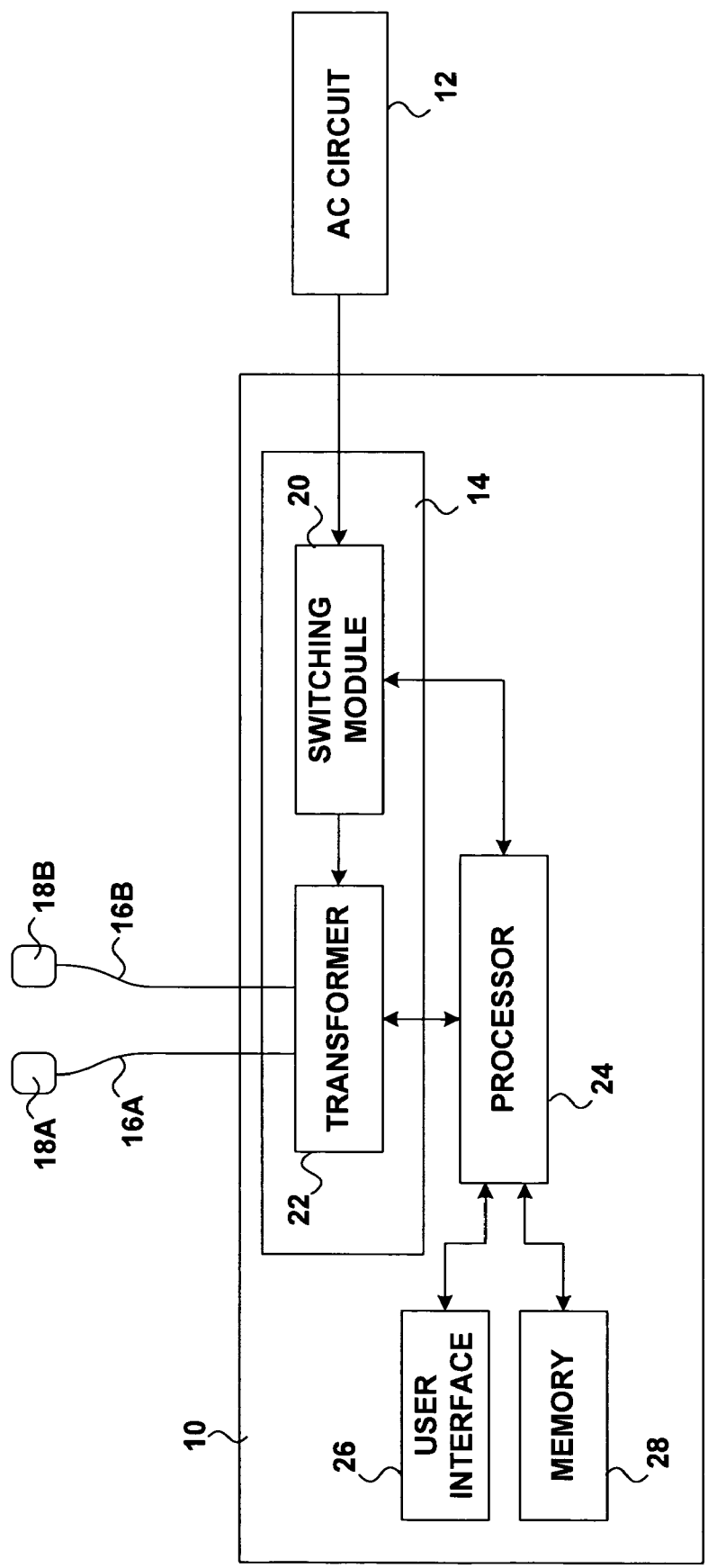
FIG. 1 is a block diagram illustrating a defibrillator that delivers energy from a circuit that is source of alternating current to a patient in the form of a defibrillation pulse.

FIG. 1 is a block diagram illustrating a defibrillator 10 that delivers energy from a circuit 12 that is source of alternating current to a patient (not shown) in the form of a defibrillation pulse. Circuit 12 may by an alternating current (ac) mains circuit, e.g., an ac circuit located within a home, office, or other building. Circuit 12 may provide alternating current at the mains voltage, which is, for example, 120 or 240 volts in the United States, 100 or 200 volts in Japan, and 110, 220, 230, or 380 volts across much of Europe. The alternating current provided by circuit 12 may be a sinusoid with a frequency of 50 or 60 hertz, depending on the country within which circuit 12 is located.

Circuit 12 may include a receptacle (not shown in FIG. 1), and defibrillator 10 may include a plug (not shown in FIG. 1) to receive energy in the form of alternating current at the mains voltage from the receptacle. Defibrillator 10 delivers the energy from circuit 12 to a patient in the form of a defibrillation pulse that is a fraction of a cycle of the alternating current sinusoid provided by circuit 12, or one or more cycles of the alternating current sinusoid. Because each of the defibrillation pulses delivered by defibrillator 10 comprises a portion of the ac sinusoid provided by circuit 12, they may be referred to as "ac defibrillation pulses." Also, defibrillator 10 does not include a battery, capacitors, or other energy storage elements to store the energy received from circuit 12 prior to delivering the energy to a patient as a defibrillation pulse. Consequently, the delivery of energy from circuit 12 to a patient by defibrillator 10 may be said to be "direct," in the sense that the energy is not stored for a significant amount of time prior to delivery to the patient.

Defibrillator 10 includes a therapy delivery module 14 that receives energy from circuit 12. Therapy delivery module 14 may deliver defibrillation pulses to a patient via conductors 16A and 16B (collectively "conductors 16") and electrodes 18A and 18B (collectively "electrodes 18") based on the energy received from circuit 12. In the illustrated embodiment, therapy delivery module 16 includes a switching module 20 and transformer 22.

Under the control of a processor 24, switching module 20 couples transformer 22 to circuit 12. Transformer 22 delivers current to a patient via conductors 16 and electrodes 18 at a stepped up voltage relative to the voltage of the alternating current received from circuit 12. Processor 24 controls the turns ratio of transformer 22, e.g., via a one or more switches (not shown) configured to select between multiple primary or secondary windings, thereby controlling the voltage or current delivered from transformer 22 to the patient. Further, through control of switching module 20, processor 24 controls the duration of the delivered defibrillation pulses, i.e., the fraction or number of cycles of alternating current at the stepped up voltage delivered to the patient. In this manner, processor 24 may be said to use switching module 20 to truncate the sinusoidal ac waveform provided by circuit 12.

With regard to its interaction with a user, defibrillator 10 may act as a manual defibrillator or an automated external defibrillator (AED) in the manner known in the art. Processor 24 controls the voltage and, in some cases, duration of a defibrillation pulse based on an energy level selected for the pulse. In embodiments in which defibrillator 10 acts as a manual defibrillator, a user may select the energy level for the defibrillation pulse via a user interface 26. In embodiments in which defibrillator 10 acts as an AED, processor 24 may select the energy level based on a schedule or progression of energy levels stored in a memory 28. In either case, a user may initiate delivery of the defibrillation pulse at the selected energy level through interaction with user interface 26.

User interface 26 may include a one or more lights, such as LEDs, a display, such as a cathode ray tube (CRT) display, LED display, or liquid crystal display (LCD), a speaker, and user input devices, such as a keypad or pointing device. Processor 24 may include any one or more of a microprocessor, digital signal processor (DSP), application specific integrated circuit (ASIC), field-programmable gate array (FPGA), or other digital logic circuitry. In some embodiments, memory 28 stores program instructions that, when executed by processor 24, cause the processor to perform the functions attributed to it herein. Memory 28 may include any magnetic, electronic or optical media, such as one or more of a random access memory (RAM), read-only memory (ROM), CD-ROM, electrically erasable programmable ROM (EEPROM), or flash memory.

FIGS. 2A-2D are timing diagrams illustrating examples of defibrillation pulses 30A-30D (collectively "defibrillation pulses 30") that may be delivered by defibrillator 10. The pulse widths of defibrillation pulses 30A and 30B are approximately equal to one cycle of the ac current sinusoid provided by circuit 12, while the pulse widths of defibrillation pulses 30C and 30D is less than one cycle and, more particularly, approximately three-quarters of one cycle. As indicated above, processor 24 of defibrillator 10 may control switching module 20 to cause transformer 22 to outputs pulse of any width, e.g., may truncate the sinusoidal ac waveform provided by circuit 12 to any number of cycles or a fraction of a cycle.

Figure 2A:
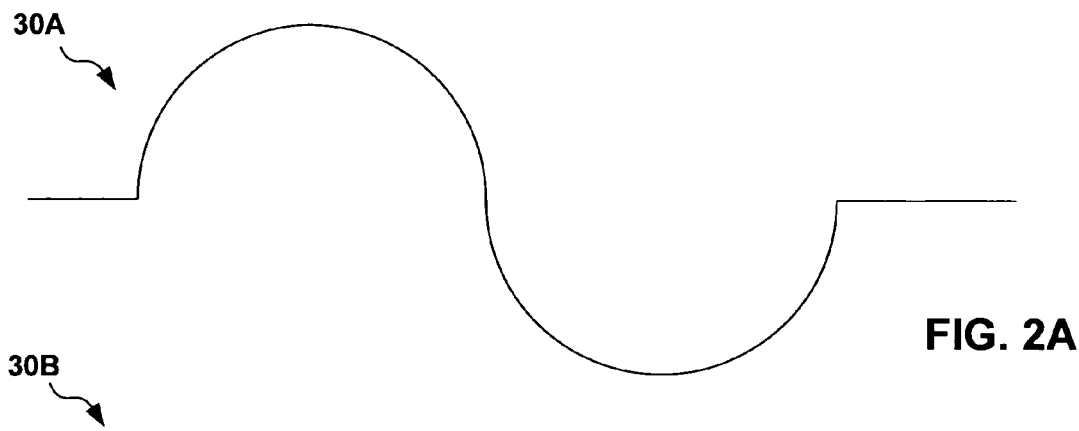
FIGS. 2A-2D are timing diagrams illustrating examples of defibrillation pulses that may be delivered by the defibrillator of FIG. 1.
Figure 2B:
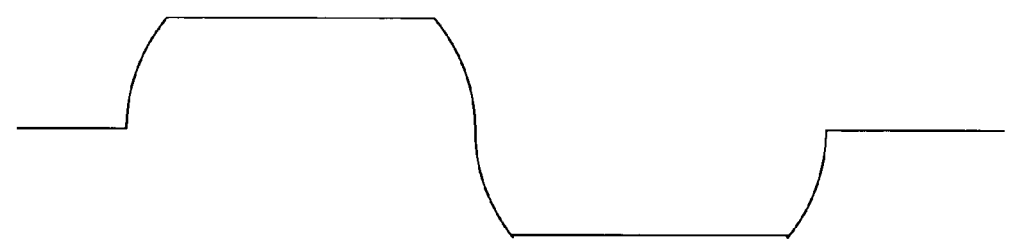
Figure 2C:
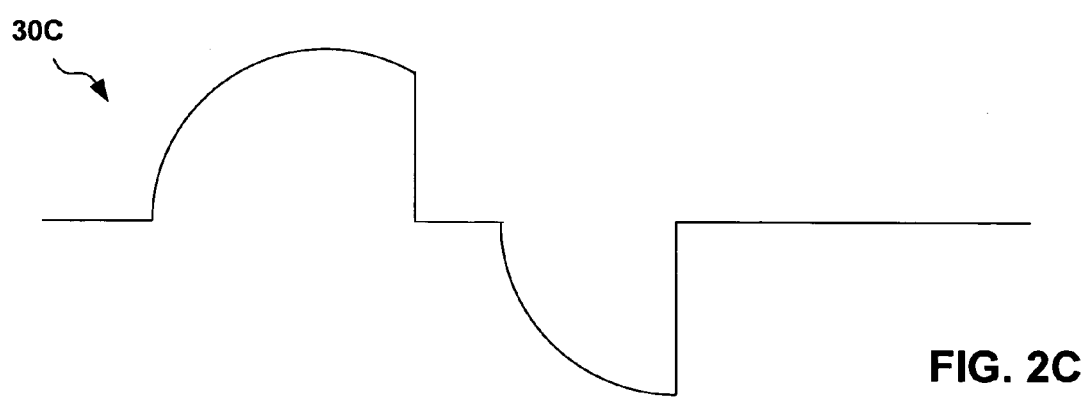
Figure 2D:
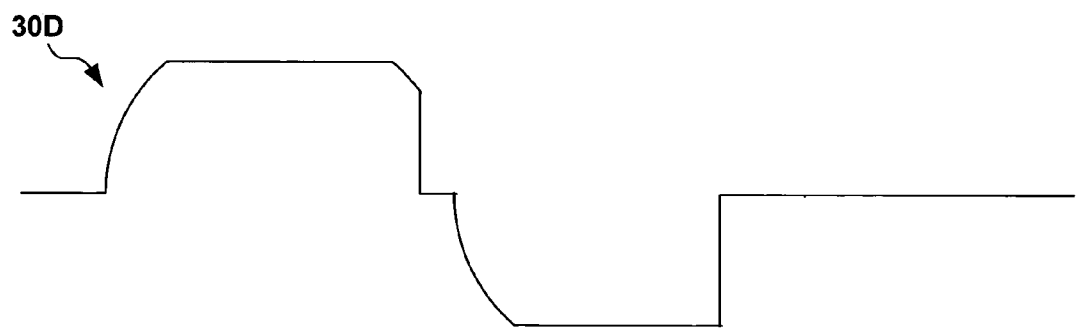

Further, as can be seen in FIGS. 2C and 2D, processor 24 may control switching module 20 to control the morphology of pulses 30, which may be desirable for defibrillation efficacy or other reasons. For example, for defibrillation pulses 30C and 3D, processor 24 controls switching module 20 to truncate the sinusoid for a period during the pulse, and controls the width of pulses 30 to be less than a full cycle. Additionally, as illustrated by pulses 30B and 30D of FIGS.

2B and 2D, respectively, processor 24 may control switching module 20 to compensate for a high resistance power circuit, delivering a "browned out" pulse to the patient. Using these techniques, defibrillator 10 may be able to output pulses 30 that resemble and have similar efficacy to the truncated exponentially decaying monophasic, biphasic, or multiphasic pulse output by commercially available defibrillators.

Figure 3A:
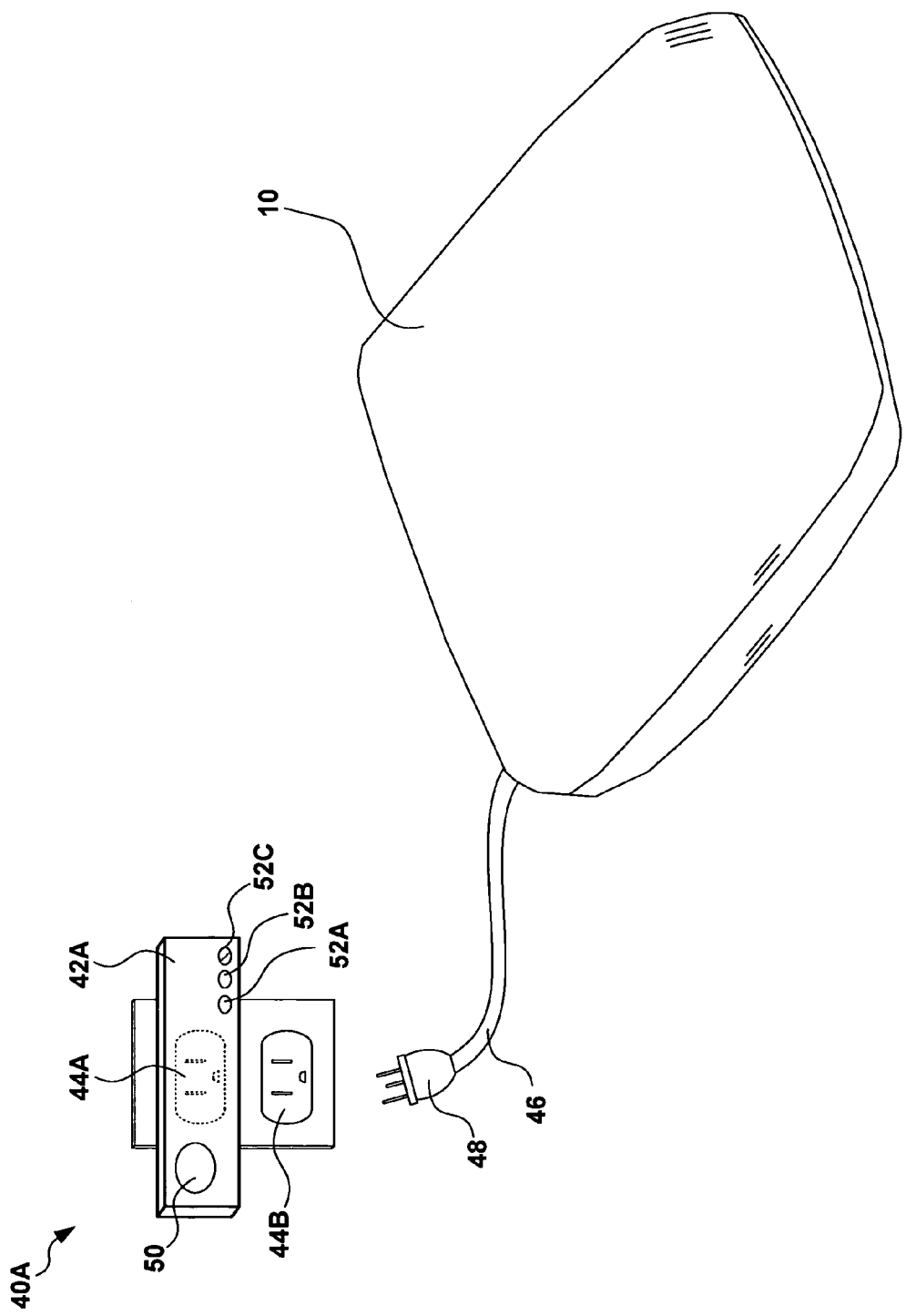
FIGS. 3A and 3B are conceptual diagrams illustrating example systems, each of which includes an example device that tests the ability of a circuit to support defibrillation by the defibrillator of FIG. 1.
Figure 3B:
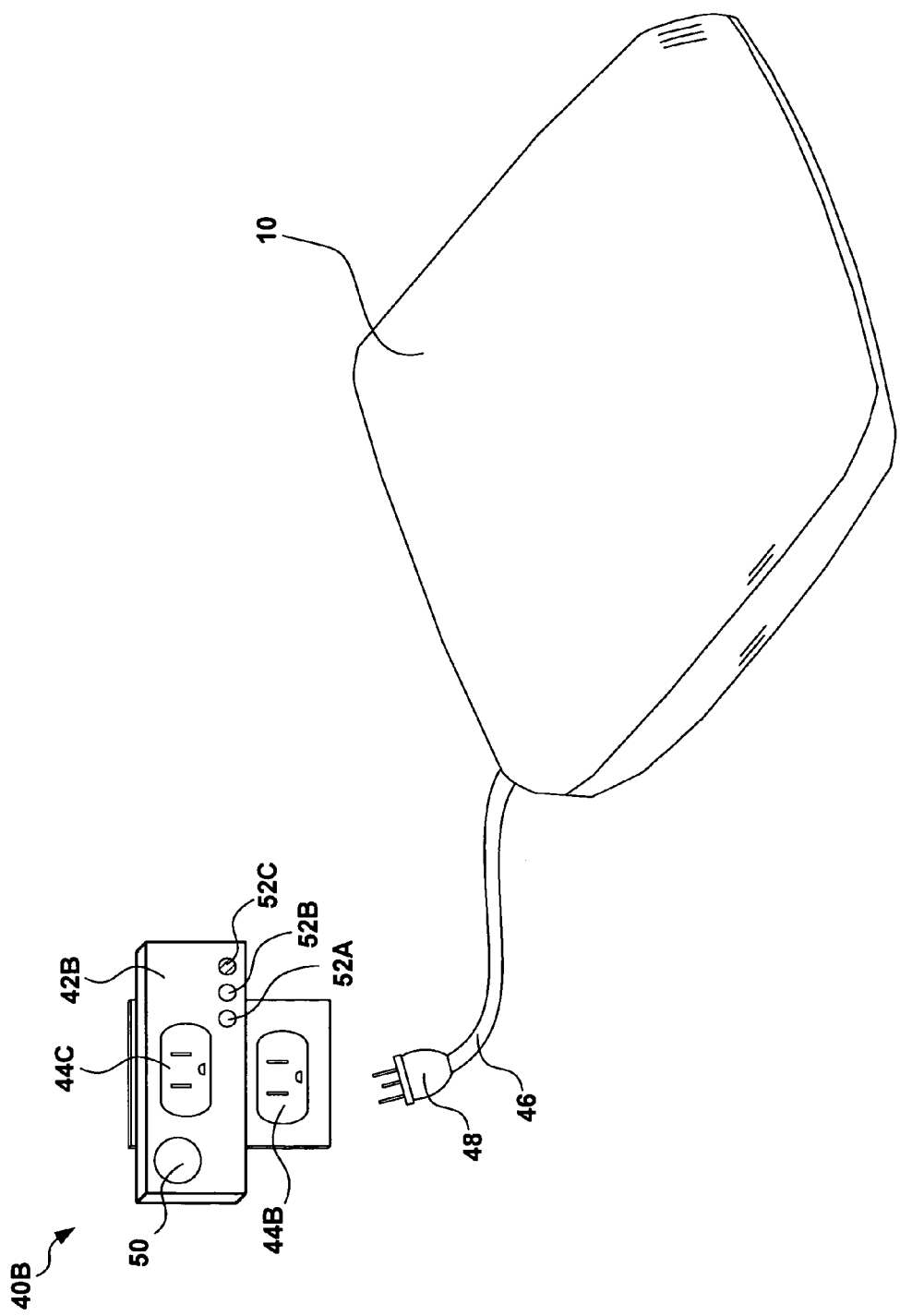

FIGS. 3A and 3B are conceptual diagrams illustrating systems 40A and 40B (collectively "systems 40"), which include devices 42A and 42B (collectively "devices 42"), respectively. Devices 42 test the ability of circuit 12 (not shown in FIGS. 3A and 3B) to support defibrillation by defibrillator 10. By testing circuit 12 for compatibility with defibrillator 10, devices 40 may allow one to determine whether the circuit is able to support defibrillation and, importantly, to make this determination before the defibrillator is needed to treat a patient.

As discussed above, circuit 12 may be, for example, a standard 120 volt, 60 Hz ac mains circuit within a residence, business, or other building. Circuit 12 includes one or both of receptacles 44A and 44B (collectively "receptacles 44"). In other words, receptacles 44 may be coupled to the same circuit 12, or different circuits 12 within the building. These receptacles 44 may be electrical wall outlets one commonly finds in a house or other building.

Defibrillator 10 includes a cord 46 with a plug 48 at its distal end for receipt by one of receptacles 44. Cord 46 and plug 48 may be a standard electrical power cord and 2-prong or 3-prong plug of the kind typically used on electrical appliances. When plug 48 is received by one of receptacles 44, defibrillator 10 receives energy from the circuit 12 coupled to that receptacle, and is capable of delivering one or more defibrillation pulses to a patient based on the energy received from the circuit in the manner described above.

In order to test circuits 12 for compatibility with defibrillator 10, each of devices 42 shown in FIGS. 1A and 1B also includes a plug (not shown) for receipt by receptacles 44. When plugged into one of receptacles 44, devices 42 may test the circuit coupled to that receptacle by applying a load to the circuit, as will be described in greater detail below. Devices 42 may test the circuit automatically upon being plugged into the receptacle, or in response to a request received from a user via a user interface. For example, the user may press button 50 of devices 42 to cause the device to test the circuit. In either case, devices 42 may be plugged into a plurality of receptacles 44 to test a plurality of circuits within a location, allowing one to identify circuits that will support defibrillation.

Devices 42 may indicate to the user whether a circuit 12 is compatible with defibrillation via the user interface. For example, devices 42 may indicate whether a circuit 12 is compatible with defibrillation by lighting one or more of lights 52A, 52B and 52C (collectively "lights 52") shown in FIGS. 1A and 1B. Lights 52 may be, for example, light emitting diodes (LEDs). In some embodiments, the user interface of a device 42 may additionally or alternatively include a display or a speaker to provide a visual or audible indication of whether the circuit is compatible with defibrillation. Further, in some embodiments, devices 42 may include a data interface, and provide an indication of whether the circuit is compatible with defibrillation via the data interface. For example, the data interface may be a network interface, and devices 42 may provide such an indication to a computer of a remote monitoring or alarm service via a network.

When a user has identified one or more circuits 12 that support defibrillation, and chosen a circuit 12 to couple defibrillator 10 to, devices 42 may remain coupled to the chosen circuit to monitor the circuit for continued defibrillation compatibility. The resistance of a circuit 12 that was initially determined to be able to support defibrillation can increase over time due to, for example, degradation of materials. At some point, the increasing resistance of the circuit may render it unable to provide adequate energy for defibrillation. Devices 12 may periodically test the circuit, e.g., periodically couple a load to the circuit, to determine whether its resistance has increased over time such that it is no longer able to deliver adequate energy for defibrillation.

However, it may also be preferable to have defibrillator 10 coupled to the chosen circuit 12 at all times, so that it is powered on and ready to be used in the case of an emergency, and able to periodically perform self-tests of its therapy delivery circuitry. Consequently, in some embodiments, it may be preferable to have a device 42 and defibrillator 10 simultaneously coupled to the circuit 12. If receptacles 44A and 44B are coupled to the same circuit 12, the device and defibrillator may be plugged into to respective ones of the receptacles. For example, device 42A may be plugged into receptacle 44A as shown in FIG. 1A, and plug 48 of defibrillator 10 may be plugged into receptacle 44B. In other embodiments, the device and defibrillator may be simultaneously plugged into a common receptacle. For example, in the embodiment illustrated in FIG. 1B, device 42B is plugged into receptacle 44A, and includes a receptacle 44C to receive plug 48 of defibrillator 10.

Figure 4A:
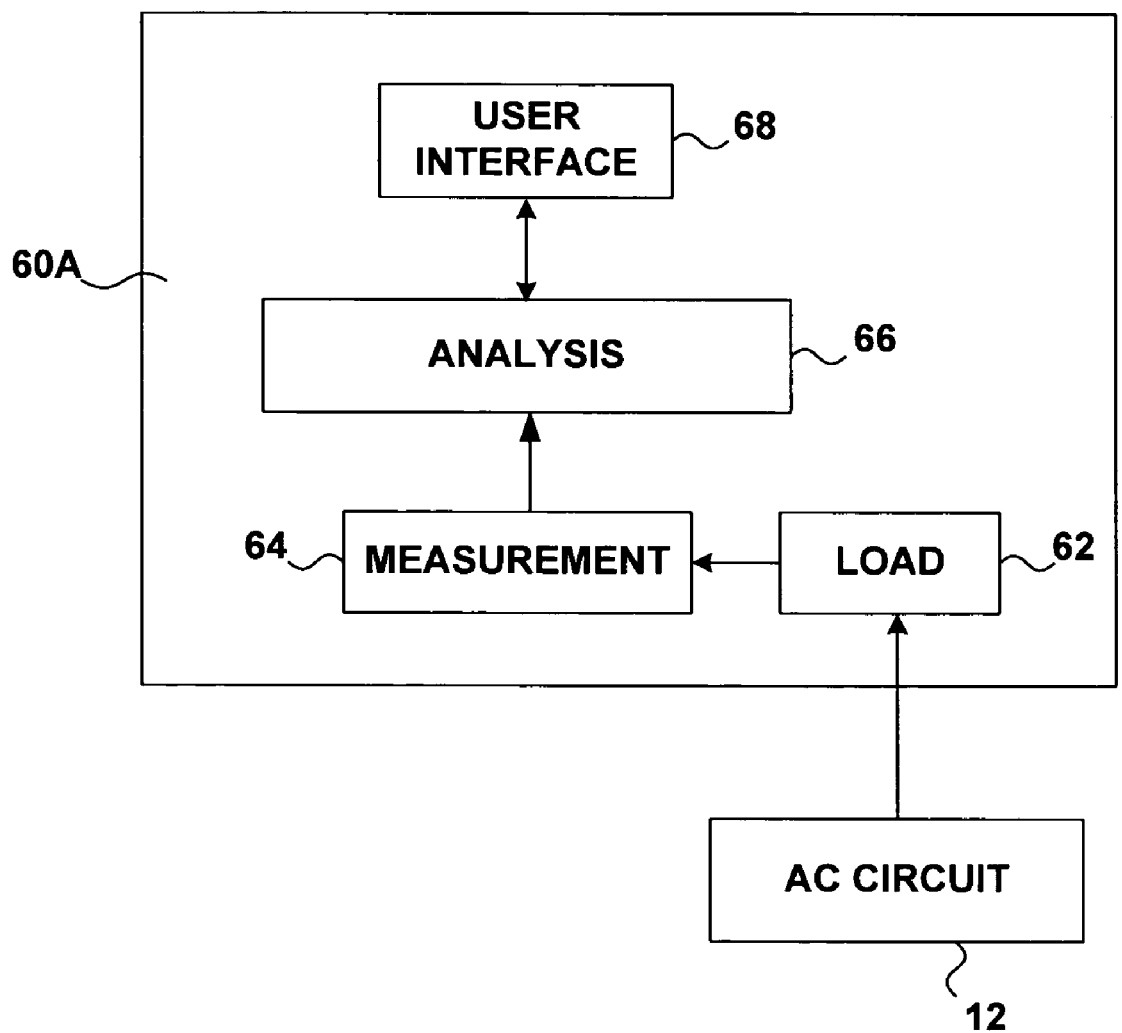
FIGS. 4A and 4B are block diagrams illustrating example devices that test the ability of a circuit to support defibrillation by the defibrillator of FIG. 1.
Figure 4B:
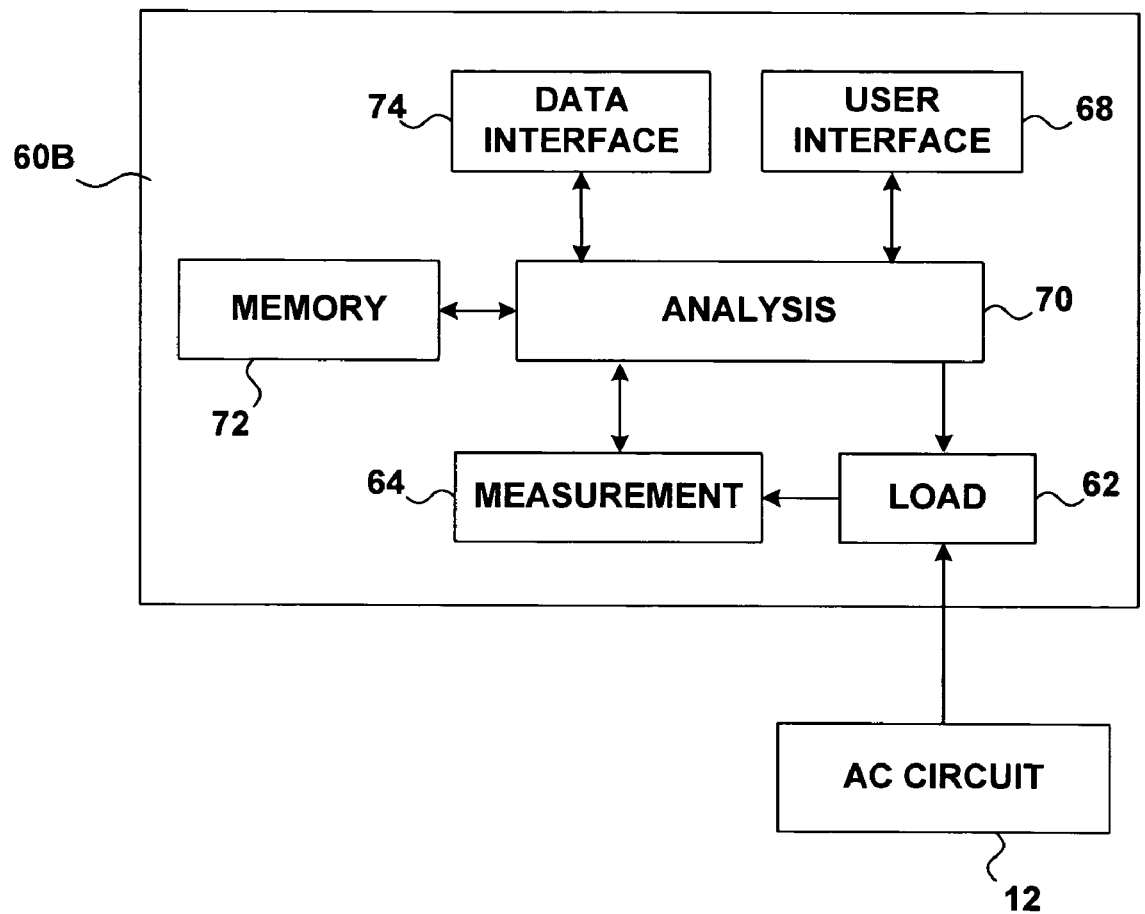

FIGS. 4A and 4B are block diagrams illustrating example devices 60A and 60B (collectively "devices 60") that test the ability of a circuit 12 to support defibrillation by defibrillator 10 (not shown in FIGS. 4A and 4B). Devices 60 may correspond to either of devices 42 illustrated in FIGS. 3A and 3B. As discussed above with reference to those Figures, devices 60 and defibrillator 10 may be coupled to circuit 12 at the same time, or different times.

Device 60A includes a load 62, e.g., one or more resistors, which may be applied to circuit 12 when device 60A is plugged into a receptacle. Alternatively, device 60A may include switches (not shown) that are responsive to depression of a button 50 (FIGS. 3A and 3B), a keypad, or the like, to couple load 62 to circuit 12. The button, keypad or the like may be part of a user interface 68 of the device.

In either case, a measurement module 64 measures values of one or more electrical parameters, such as voltage, current, or resistance, when load 62 is coupled to circuit 12. Measurement module 64 may include an ac voltmeter, for example, to measure one or more voltage values. Based on the values of one or more electrical parameters measured by measurement module 64, an analysis module 66 determines whether circuit 12 is able to support defibrillator 10, and then provides an indication to a user of whether circuit 12 is able to support defibrillator 10 via a user interface 68.

For example, analysis module 66 may include analog circuitry that compares a signal received from the measurement module, which reflects the value of the electrical parameter measured by the measurement module, to a threshold. In such embodiments, user interface 68 may include one or more lights 52 (FIGS. 3A and 3B) or an audible alarm, and the analog circuitry may output a signal based on the comparison that drives the light or alarm. In this manner, analysis module 66 may indicate to a user whether circuit 12 is capable of providing adequate energy for defibrillation by defibrillator 10.

In addition to load 62, measurement module 64, analysis module 70 and user interface 68, device 60B of FIG. 6B includes a memory 72 and a data interface 74. In the embodiment illustrated in FIG. 6B, analysis module 70 may take the form of a processor that is capable of accessing memory 72, and transmitting data via data interface 74. The processor may include any one or more of a microprocessor, DSP, ASIC, FPGA, or other digital logic circuitry.

In such embodiments, analysis module 70 may control application of load 62 to circuit 12, e.g., selectively apply the load to the circuit, to determine whether the circuit is able to provide adequate energy to support defibrillation by defibrillator 10. Analysis module 70 may also control measurement module 64 to measure of the electrical parameter value when load 62 is applied to circuit 12. Further, in such embodiments, analysis module 70 may determine whether circuit 12 is capable of supporting defibrillator 10 by comparing the measured electrical parameter value to a threshold value stored in memory 72. Alternatively, analysis module 70 may determine whether circuit 12 is capable of supporting defibrillator 10 by processing one or more measured electrical parameter values to determine another value that may then be compared to a threshold value, as will be described in greater detail below.

Based on the determination, analysis module 70 indicates to a user whether circuit 12 is able to support defibrillator 10. For example, analysis module 70 may provide the indication to the user via user interface 68, which may include lights 52, a display, such as a CRT, LED or LCD display, or a speaker. In some embodiments, analysis module 70 controls the coupling of load 62 to circuit 12 and/or the measurement of the electrical parameter value by measurement module 64 in response to receiving a request from a user via user interface 68, which may include one or more buttons 22 (FIG. 1) or a keypad that allow the user to make such a request.

Device 60B may include data interface 74 in addition to, or as an alternative to user interface 68. Analysis module 70 may provide the indication of whether circuit 12 supports defibrillator 10 to another device, such as a computing device, via data interface 74, and the other device may provide the indication to the user. Data interface 74 may include, for example, a network interface, and the other device may be a remote computing device that analysis module 70 communicates with via a network. In some embodiments, for example, device 60B may monitor circuit 12 over a period of time, and analysis module 70 may indicate to a device of a remote monitoring or alarm service whether circuit 12 continues to be able to provide adequate energy for defibrillation via data interface 74.

In some embodiments, memory 72 stores program instructions that, when executed by a processor of analysis module 70, cause the processor to perform the functions attributed to analysis module 70 herein. Accordingly, the invention also contemplates computer-readable media storing instructions to cause a processor to provide the functionality described herein. Memory 72 may include any magnetic, electronic or optical media, such as one or more of a RAM, ROM, CD-ROM, EEPROM, or flash memory.

Figure 5:
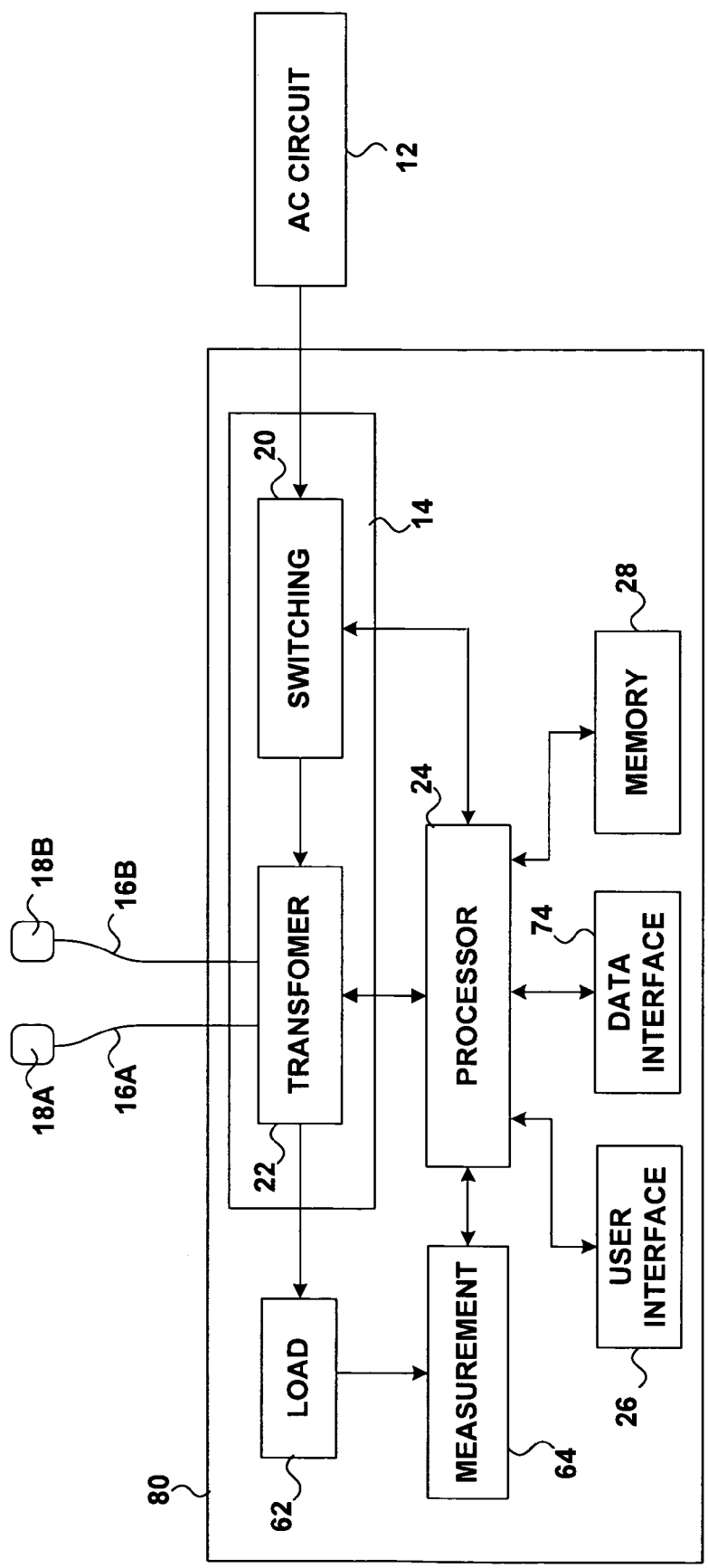
FIG. 5 is block diagram illustrating a defibrillator that is capable of delivering energy from a circuit that is source of alternating current to a patient in the form of a defibrillation pulse, and tests the ability of the circuit to support defibrillation.

FIG. 5 is block diagram illustrating a defibrillator 80 that is capable of delivering energy from a circuit 12 to a patient in the form of a defibrillation pulse, like defibrillator 10 of FIG. 1, and also tests the ability of the circuit to support defibrillation. Although the embodiments illustrated by FIGS. 3A, 3B, 4A and 4B depict a separate device 42, 60 that tests circuit 12 for compatibility with defibrillation, the invention is not so limited. In other embodiments, such as the embodiment illustrated in FIG. 5, a defibrillator itself tests the ability of circuit 12 to support defibrillation.

Like defibrillator 10 of depicted in FIG. 1, defibrillator 80 includes a therapy delivery module 14 with a switching module 20 and transformer 22, a processor 24, a user interface 26 and a memory 28. These components of defibrillator 80 may be substantially the same as the like numbered components of defibrillator 10 described above with reference to FIG. 1. Defibrillator 80 also includes a load 62, a measurement module 64 and a data interface 74, which may be substantially the same as the like numbered components of device 60B described above with reference to FIG. 4B. Processor 24 of defibrillator 80 may act as an analysis module with respect to the circuit testing function of defibrillator 80, e.g., provide the functionality ascribed analysis module 70 described above with reference to FIG. 4B.

In some embodiments, processor 24 controls application of load 62 directly to circuit 12, e.g., in parallel with switching module 20. In such embodiments, defibrillator 80 may employ substantially the same techniques described herein as being employed by devices 60 for determining whether circuit 12 is compatible with defibrillation. In the illustrated embodiment, on the other hand, processor 24 controls application of load 62 indirectly to circuit 12 by controlling coupling of load 62 to therapy delivery module 14 and, more particularly, transformer 22.

Upon controlling the coupling of load 62 to therapy delivery module 14, processor 24 controls the therapy delivery module to deliver a defibrillation pulse to load 62. Processor 24 also controls measurement module 64 to measure a value of at least one electrical parameter during delivery of the defibrillation pulse to load 62. Processor 24 determines whether circuit 12 is able to support defibrillation based on the electrical parameter value, e.g., based on comparison of the electrical parameter value to a threshold value stored in memory 28. Processor 24 may provide an indication to a user of whether circuit 12 is able to support defibrillation when defibrillator 80 is inactive, shortly before defibrillator 80 is to be used to treat a patient, or during treatment of patient with defibrillator 80. As indicated above, measurement module 64 may include, for example, an ac voltmeter and measure the voltage across load 62 when the defibrillation pulse is delivered to the load.

Figure 6:
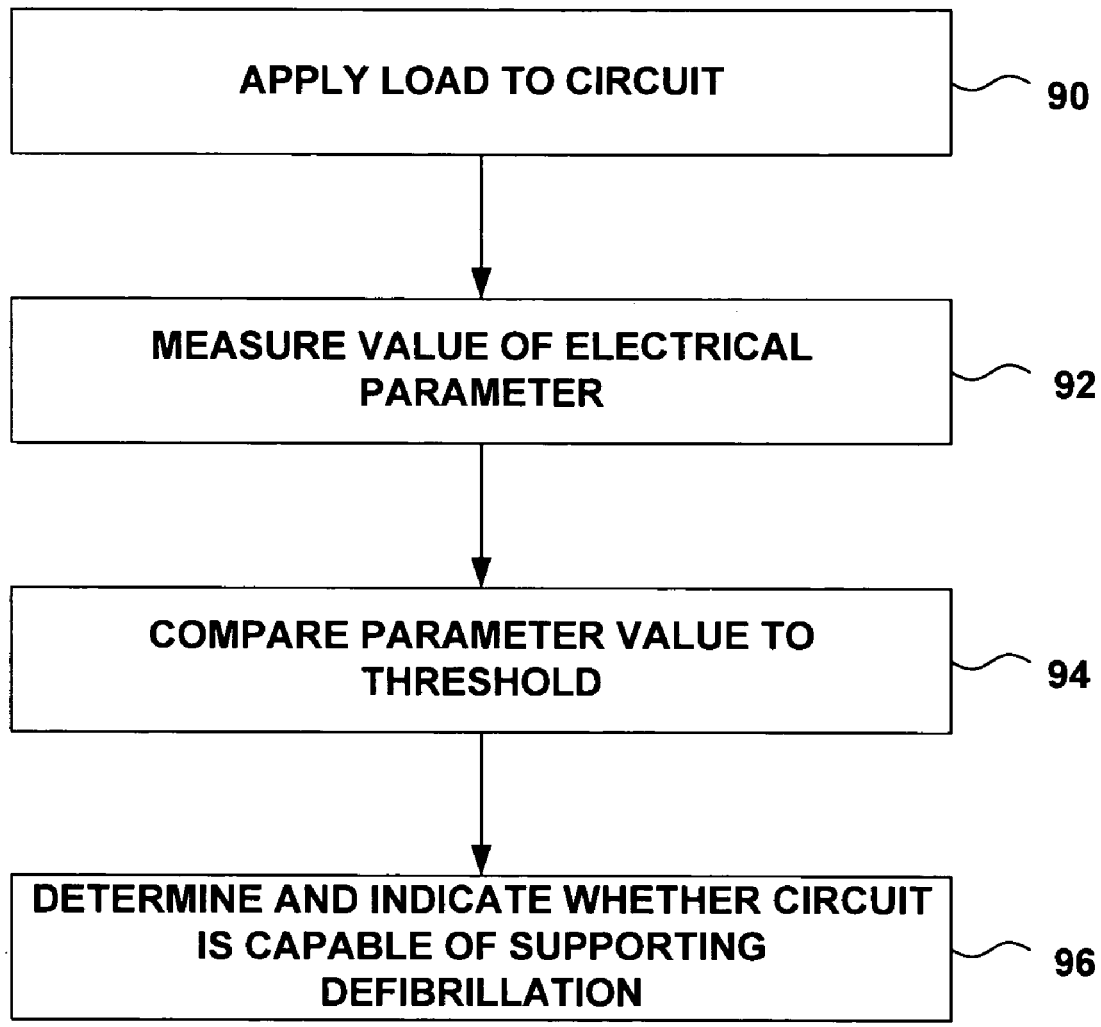
FIG. 6 is a flow diagram illustrating an example method for testing the ability of a circuit to support defibrillation.

FIG. 6 is a flow diagram illustrating an example method for testing the ability of a circuit 12 to support defibrillation. Although the method is described primarily with reference to a device 42, 60, it is understood that a defibrillator 80 may also perform the method illustrated by FIG. 4. As described in greater detail above, the method may be performed automatically upon coupling of the device 42, 60 to the circuit 12, in response to a request from a user, or periodically so long as the device is coupled to the circuit.

According to the example method, a load 62 is applied to the circuit 12 (90), and a measurement module 64 measures a value of at least one electrical parameter when the load is applied to the circuit (92). For example, measurement module 64 may measure the voltage across the load 62 when the load is applied to the circuit. An analysis module 66, 70 then compares the measured value to a threshold value (94), determines whether the circuit 12 is capable of providing adequate energy to support defibrillation by a defibrillator 10 based on the comparison, and provides an indication of the determination to a user (96).

In some embodiments in which the measurement module measures the voltage across the load when applied to the circuit, the analysis module may determine the amount of current provided by the circuit when the load is applied to the circuit based on the measured voltage and the known resistance of the load. In such embodiments, rather than comparing the measured voltage to a threshold value, the analysis module may compare the determined current to a threshold current value known to be adequate for supporting defibrillation, such as 400 amps. In other embodiments, the measurement module may include circuitry to directly measure the current output by the circuit when the load is applied to the circuit.

Figure 7:
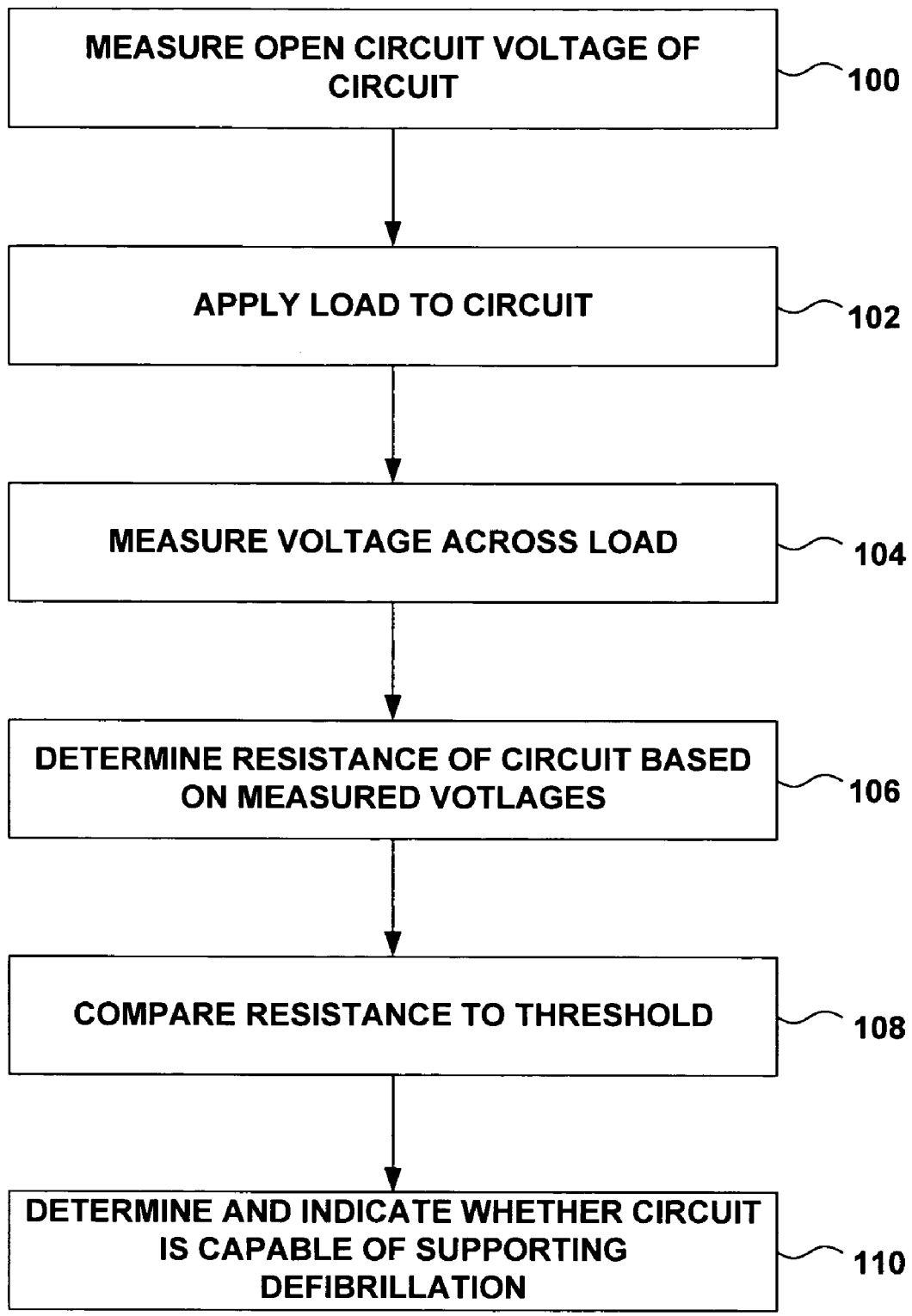
FIG. 7 is a flow diagram illustrating another example method for testing the ability of a circuit to support defibrillation.

FIG. 7 is a flow diagram illustrating another example method for testing the ability of a circuit 12 to support defibrillation. Again, although the method is described primarily with reference to a device 42, 60, it is understood that a defibrillator 80 may also perform the method illustrated by FIG. 5. As described in greater detail above, the method may be performed automatically upon coupling of the device to the circuit, in response to a request from a user, or periodically so long as the device is coupled to the circuit.

According to the example method, a measurement module 64 measures an open circuit voltage of the circuit 12, i.e., when a load 62 is not applied to the circuit (100). When the load 62 is applied to the circuit 12 (102), the measurement module 64 measures the voltage across the load (104). The open circuit voltage and the voltage across the load 62 may be measured in any order.

Based on the open circuit voltage and the voltage across the load 62, an analysis module 70 determines the resistance of the circuit 12 (106). In particular, the analysis module may use equation (1) to determine the resistance of the circuit 12 ($R_{circuit}$) based on the voltage across the load 62 ($V_{load}$), the open circuit voltage ($V_{open}$), and the known resistance of the load ($R_{load}$). Equation (1) may be stored in memory 72 of the device.

$$R_{circuit}=(V_{open}V_{load})*R_{load}/V_{load} \quad (1)$$

The analysis module may then compare the resistance of the circuit to a threshold resistance value associated with the ability of the circuit 12 to deliver adequate energy to support defibrillation, such 0.1 ohm (108). The analysis module determines whether the circuit supports defibrillation based on the comparison, and provides an indication of the determination to a user (110). The threshold value may also be stored in the memory 72.

Figure 8:
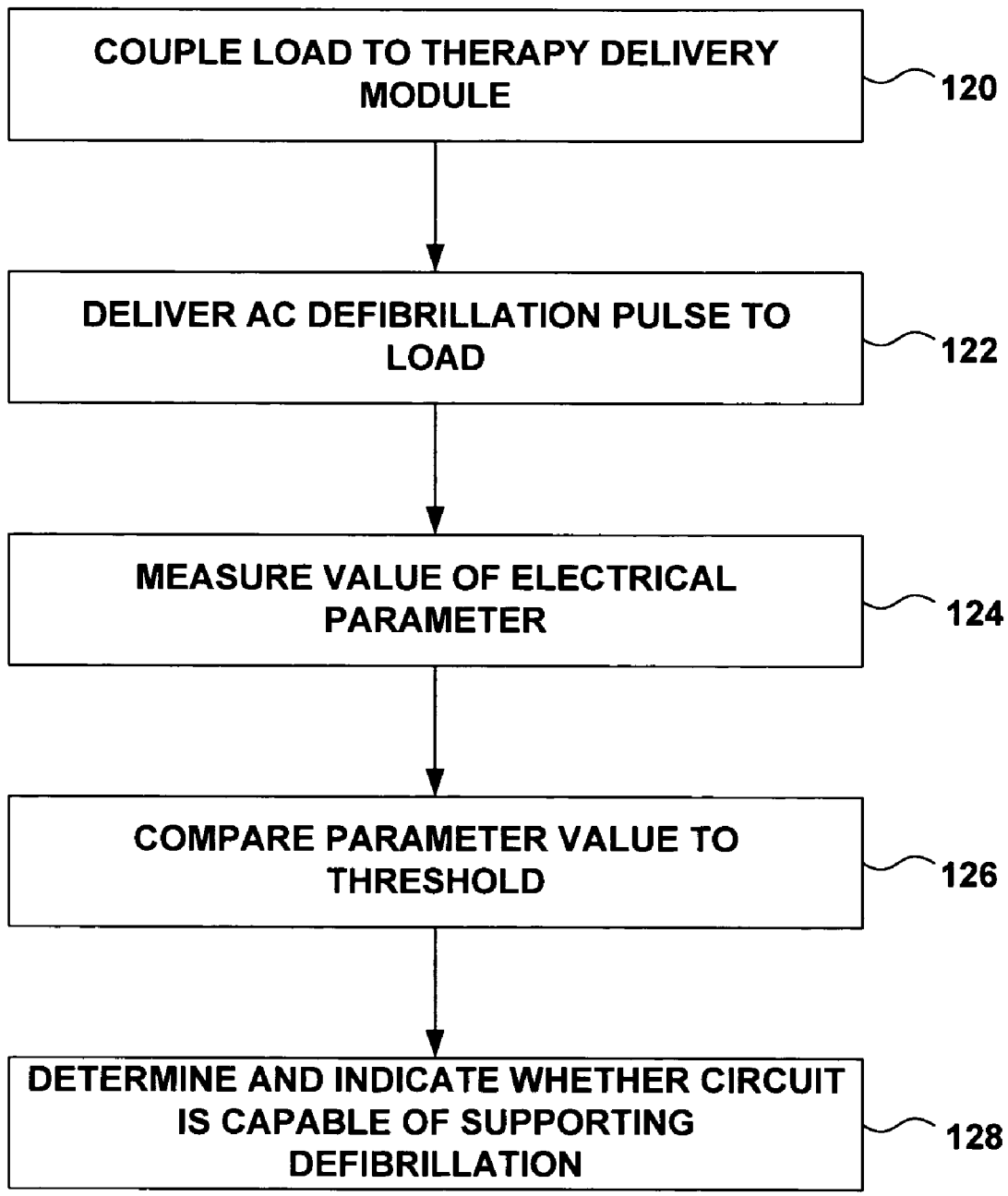
FIG. 8 is a flow diagram illustrating an example method for testing the ability of a circuit to support defibrillation that may be employed by a defibrillator.

FIG. 8 is a flow diagram illustrating an example method for testing the ability of a circuit 12 to support defibrillation that may be employed by a defibrillator 80. As described in greater detail above, the method may be performed automatically upon coupling of the defibrillator to the circuit, in response to a request from a user, or periodically so long as the defibrillator is coupled to the circuit.

According to the example method, a processor 24 of the defibrillator 80 controls coupling of a load 62 to a therapy delivery module 14 of the defibrillator (120), and delivery of a defibrillation pulse from the therapy delivery module 14 to the load 62 (122). The defibrillator 80 includes a measurement module 64 that measures one or more electrical parameters, such as voltage, current or resistance, and the processor 24 controls the measurement module 64 to measure at least one such electrical parameter during delivery of the defibrillation pulse to the load 62 (124). The processor 24 compares the measured value of the electrical parameter to a threshold value (126), determines whether determines whether the circuit supports defibrillation based on the comparison, and provides an indication of the determination to a user (128). The threshold value may be stored in a memory 28 of the defibrillator, and the processor 24 may provide the indication via one or both of a user interface 26 or data interface 74 of the defibrillator.

For example, the measurement module 64 may measure the voltage across the load 62 during delivery of the defibrillation pulse. The voltage measured across load 62 during delivery of a defibrillation pulse will indicate whether the defibrillation pulse had an adequate energy level for defibrillation of a patient, and thereby indicate whether the provided adequate energy to support defibrillation. Processor 24 may, for example, adjust the turns ratio of a transformer 22 of the therapy delivery module 14 such that the therapy delivery module 14 delivers the defibrillation pulse at a voltage associated with a maximum desired defibrillation pulse energy level. The processor 24 may then compare the voltage measured across the load 62 by measurement module 64 to a voltage threshold value associated with the maximum desired energy level to determine whether the circuit provides adequate energy to support the desired maximum energy level. The threshold voltage value may be, for example, approximately 1000 volts for a 50 ohm patient.

In other embodiments, the measurement module 64 may measure current through the load 62 during delivery of the defibrillation pulse, and the processor 24 may compare the measured current to a threshold associated with a maximum desired energy level for defibrillation pulses to determine whether circuit 30 provides adequate energy to support defibrillation. Further, in addition to determining whether the circuit 12 is compatible with defibrillation, the processor 24 may also determine whether the therapy delivery module 14 is functioning properly, i.e., perform a diagnostic self-test of the therapy delivery module, based on one or more electrical parameter values measured by measurement module 64 during delivery of a defibrillation pulse to the load by the therapy delivery module. The processor may indicate to a user whether the circuit is able to provide adequate energy for defibrillation and/or whether the therapy delivery module is functioning properly via one or both of a user interface 26 and data interface 72.

Figure 9:
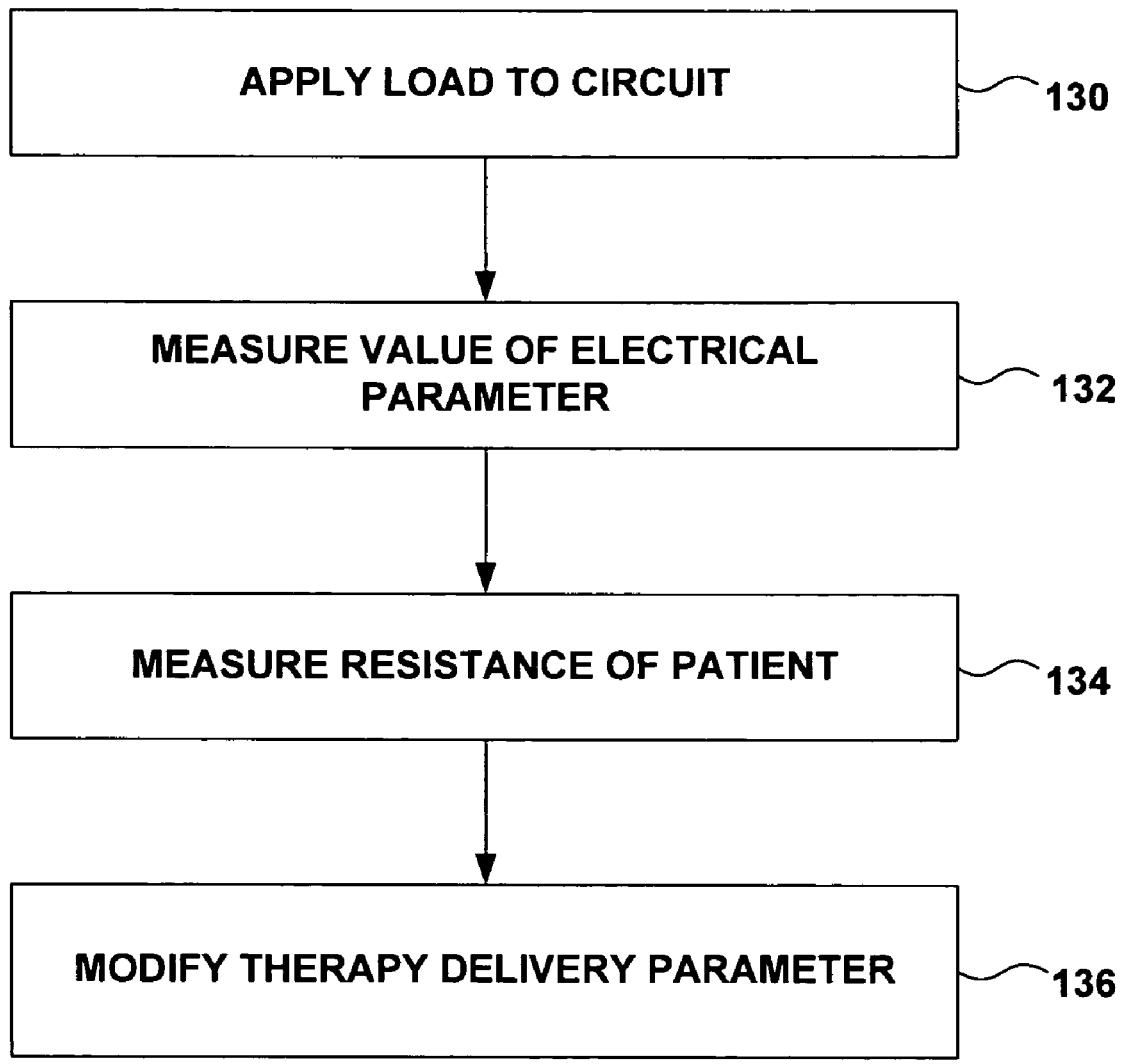
FIG. 9 is a flow diagram illustrating an example method that may be employed by a defibrillator to modify a therapy delivery parameter in order to deliver defibrillation pulses at an energy level supported by a circuit.

FIG. 9 is a flow diagram illustrating an example method that may be employed by a defibrillator 80 to modify a therapy delivery parameter, such as defibrillation pulse voltage or duration, in order to deliver defibrillation pulses at an energy level supported by a circuit 12. A processor 24 of the defibrillator 80 controls application of a load 62 to the circuit 12 (130), and measurement of an electrical parameter during application of the load by a measurement module 64 (132), using any of the techniques described above. For example, the processor 24 may control delivery of a defibrillation pulse to the load, and measurement of the voltage across the load during delivery of the defibrillation pulse, as described above with reference to FIG. 8.

In some embodiments, the processor 24 modifies one or more therapy delivery parameters based on the measured value of the electrical parameter (136). For example, the processor 24 may apply an equation or look-up table to the measured value to determine a modification to the turns ratio of a transformer 22 of the therapy delivery module 14. By modifying the turns ratio, the processor 24 may modify the current drawn by the patient, or other load, during delivery of a defibrillation pulse to a level supported by the circuit.

Because the current drawn by the patient is directly related to the turns ratio, the processor 24 may decrease the turns ratio if the measured electrical parameter value indicates that the circuit 12 is unable to provide adequate energy for the current turns ratio. However, decreasing the turns ratio of the transformer decreases the stepped up voltage provided by the transformer and, consequently, the current delivered to the patient. Therefore, in some embodiments, the processor 24 may additionally modify the programmed duration of defibrillation pulses, which the processor 24 controls via switching module 20, so that the amount of energy delivered to the patient remains substantially the same after modification of turns ratio. Processor 24 may modify the duration of the defibrillation pulse to, for example, include a greater number of cycles of the sinusoidal ac waveform provided by the circuit, or a greater fraction of a single cycle, within the pulse.

In other embodiments, the processor 24 additionally controls the measurement module 64 to measure one or more electrical parameters that enable the processor to determine a resistance of a patient (134). The amount of current drawn from the circuit by the transformer during delivery of a defibrillation pulse is inversely related to patient resistance, which varies from patient to patient within a range from approximately 25 to approximately 150 ohms. Consequently, while the circuit may support delivery of a defibrillation pulse at a first voltage for a first patient, the circuit may not be able to support delivery of a defibrillation pulse at the first voltage for a second patient with a lower resistance than the first patient.

Therefore, in embodiments in which patient resistance is determined, the processor 24 may modify the one or more therapy delivery parameters based on both the measured value of the electrical parameter and the determined resistance of the patient, allowing the defibrillator 80 to deliver defibrillation pulses at a voltage that is supported by the circuit across a range of patient resistances (136). In such embodiments, the processor may apply one or more equations or look-up tables to one or both of the measured electrical parameter and the measured patient resistance to determine, for example, a modification of the turns ratio of the transformer, and may also adjust the defibrillation pulse duration, as discussed above.

Processor 24 may determine the patient resistance in any of a variety of ways known in the art. For example, processor 24 may control therapy delivery module 14 to deliver a low amplitude constant current to the patient via conductors 16 and electrodes 18 (FIG. 5), and measurement module 64 to measure the voltage across the patient during delivery of the constant current. Processor 24 may then determine the resistance of the patient based on the voltage measured by the measurement module 64. Using this technique, the processor 24 may determine the resistance of a patient at any time, including prior to delivery of a first defibrillation pulse to the patient. In other embodiments, the processor 24 may control the measurement module 64 to measure one or more of voltage and current during delivery of a first defibrillation pulse to a patient by the therapy delivery module 14, and the processor 24 may determine the resistance of the patient based on the measured voltage or current for adjustment of a therapy delivery parameter prior to delivery of a subsequent defibrillation pulse.

Further, in some embodiments, rather than applying a load 62, e.g., one or more resistors, to the circuit 12, the load that is applied to the circuit is the patient. In such embodiments, the processor 24 may control the measurement module 64 to measure one or more electrical parameters that indicate the capability of the circuit 12 to support defibrillation during delivery of a first defibrillation pulse from the therapy delivery module 14 to the patient. The processor 24 may then modify one or more therapy delivery parameters for delivery of a subsequent defibrillation pulse. For example the processor 24 may control the therapy delivery module to measure one or more of voltage and current during delivery of a first defibrillation pulse to a patient. The processor 24 may then determine the resistance of the patient based on the measured voltage and/or current values, and determine modifications to the turns ratio and pulse duration for a subsequent pulse based on the measured voltage and/or current, and the determined patient resistance.

Various embodiments of the invention have been described. However, one skilled in the art will appreciate that various modifications may be made to the described embodiments without departing from the scope of the invention. For example, devices and techniques for determining whether a circuit provides adequate energy to support defibrillation by a defibrillator that delivers energy from the circuit to a patient in the form of defibrillation pulses have been described. One skilled in the will appreciate that this determination may involve determinations of whether the circuit provides adequate power, current, voltage, charge, or the like. Further, as indicated herein the determination of whether the circuit provides adequate energy may involve a determination of the resistance of the circuit.

The various example threshold values for current, voltage and resistance identified herein are merely exemplary, and may be varied depending on a desired degree of defibrillator reliability and/or desired average or maximum defibrillation pulse energy levels. Further, the threshold values used by devices to determine whether a circuit will support defibrillation may be fixed, variable based on user input, or programmable by a user. Moreover, although measuring an electrical parameter to determine whether an ac circuit supports defibrillation has been described herein primarily as involving application of a load to the circuit, the invention is not so limited. Determining whether an ac circuit supports defibrillation may involve measurement of any electrical parameter of the circuit using any known techniques.

Additionally, although providing an indication of whether the circuit supports defibrillation has been described herein primarily in terms of a device lighting a light or activating an audible alarm, the invention is not so limited. In some embodiments, for example, a device may provide an indication of the maximum energy, current, or voltage level for a defibrillation pulse that the a circuit is capable of supporting, allowing the user to determine whether the circuit provides adequate energy for defibrillation based on the indicated energy, current or voltage. These and other embodiments are within the scope of the following claims.

The invention claimed is:

1. A device for determining whether or not an alternating current (AC) circuit can be expected to support a defibrillator as a source of alternating current, comprising:
   a measurement module for measuring a value of at least one electrical parameter of power received from the AC circuit in the form of alternating current, wherein the alternating current provided from the AC circuit repeatedly forces electrons in a first direction and then in a second direction opposite the first direction;
   a therapy delivery module adapted to be electrically coupled to the AC circuit and configured to deliver to a patient defibrillation energy that would be derived from the received power; and
   an analysis module to determine whether or not the defibrillation energy can be expected to be adequate for the patient to be defibrillated based on the measured electrical parameter value.

2. The device of claim 1, in which the defibrillation energy is to be delivered in the form of an alternating current that repeatedly forces electrons in a first direction and then in a second direction opposite the first direction.

3. The device of claim 1, in which the measurement module includes an alternating current voltmeter.

4. The device of claim 1, in which the analysis module includes a processor.

5. The device of claim 1, in which the measured electrical parameter value helps determine whether or not the AC circuit will be able to provide adequate current for the defibrillation energy to be expected to be adequate for the patient to be defibrillated.

6. The device of claim 1, in which the measurement module measures the electrical parameter value when a load is applied to the AC circuit.

7. The device of claim 6, in which the load includes at least one resistor.

8. The device of claim 6, in which the analysis module controls the application of the load to the circuit.

9. The device of claim 6, further comprising a user interface for a user to control the application of the load.

10. The device of claim 6, in which the measurement module measures a voltage across the load when the load is applied to the AC circuit, and the analysis module determines whether or not the defibrillation energy can be expected to be adequate based on the voltage measured across the load.

11. The device of claim 10, in which the measurement module measures an open circuit voltage of the AC circuit when the load is not applied to the AC circuit, and the analysis module determines a resistance of the AC circuit based on the open circuit voltage and the voltage measured across the load, and determines whether or not the defibrillation energy can be expected to be adequate based on the resistance.

12. The device of claim 1, further comprising a user interface for indicating whether or not the defibrillation energy can be expected to be adequate for the patient to be defibrillated.

13. The device of claim 12, in which the user interface includes at least one of a light, a display, or an audible alarm.

14. The device of claim 1, further comprising a data interface for communicating to another device whether or not the defibrillation energy can be expected to be adequate for the patient to be defibrillated.

15. The device of claim 1, in which the device includes an external defibrillator.

16. The device of claim 15, further comprising a user interface for indicating both a parameter of the therapy delivery module and whether or not the defibrillation energy can be expected to be adequate for the patient to be defibrillated.

17. The device of claim 15, in which the analysis module controls coupling of a load to the therapy delivery module, controls the therapy delivery module to deliver the defibrillation energy to the load, and controls the measurement module to measure the electrical parameter value during delivery of the defibrillation energy to the load.

18. The device of claim 17, in which the load comprises the patient.

19. The device of claim 1, in which the AC circuit includes a receptacle, and the device further comprises a plug that is configured for receipt by the receptacle to couple the device to the AC circuit.

20. The device of claim 19, in which the device further comprises a receptacle that is coupled to the AC circuit via the plug, and the receptacle receives a plug of another device to couple the other device to the AC circuit.

21. An external defibrillator, comprising:
a therapy delivery module configured to deliver defibrillation energy to a patient according to a therapy delivery parameter value, the defibrillation energy to be generated by converting power to be received from an alternating current (AC) circuit in the form of alternating current, wherein the alternating current provided from the AC circuit repeatedly forces electrons in a first direction and then in a second direction opposite the first direction;
a measurement module for measuring a value of at least one electrical parameter of the power to be received from the AC circuit; and
a processor for modifying the therapy delivery parameter value based on the measured electrical parameter value.

22. The external defibrillator of claim 21, in which the defibrillation energy is to be delivered in the form of an alternating current that repeatedly forces electrons in a first direction and then in a second direction opposite the first direction.

23. The external defibrillator of claim 21, in which the measurement module includes an alternating current voltmeter.

24. The external defibrillator of claim 21, wherein the processor controls application of a load to the AC circuit, and the measurement module measures the electrical parameter value when the load is applied to the AC circuit.

25. The external defibrillator of claim 24, wherein the measurement module measures a voltage across the load when the load is applied to the AC circuit, and the processor modifies the therapy delivery parameter value based on the voltage measured across the load.

26. The external defibrillator of claim 25,
wherein the measurement module measures an open circuit voltage of the AC circuit, and
wherein the processor determines a resistance of the AC circuit based on the open circuit voltage and the voltage measured across the load, and modifies the therapy delivery parameter value based on the resistance.

27. The external defibrillator of claim 21,
wherein the processor controls coupling of a load to the AC circuit via the therapy delivery module, controls the therapy delivery module to deliver an alternating current defibrillation pulse to the load, and
wherein the measurement module measures the electrical parameter value during delivery of the alternating current defibrillation pulse to the load.

28. The external defibrillator of claim 27, wherein the load comprises the patient, the defibrillation pulse delivered to the load comprises a first defibrillation pulse delivered to the patient according to a value of the therapy delivery parameter prior to modification, the processor modifies the therapy delivery parameter value based on the electrical parameter value measured during delivery of the first defibrillation pulse to the patient, and the processor controls the therapy delivery module to deliver a second defibrillation pulse to the patient according to the modified therapy delivery parameter value.

29. The external defibrillator of claim 21, wherein the processor modifies the therapy delivery parameter value based on the measured electrical parameter value to modify a current draw of the therapy delivery module during delivery of the defibrillation energy to the patient.

30. The external defibrillator of claim 21, wherein the therapy delivery module includes a transformer that increases a voltage of alternating current provided by the circuit for delivery of the defibrillation energy to the patient, and the processor modifies a voltage of alternating current output by the transformer based on the measured electrical parameter value.

31. The external defibrillator of claim 30, wherein the processor modifies a turns ratio of the transformer based on the measured electrical parameter value.

32. The external defibrillator of claim 21, wherein the defibrillation energy comprises a defibrillation pulse, the processor modifies a duration of the defibrillation pulse based on the measured electrical parameter value.

33. The external defibrillator of claim 21, wherein the processor determines a resistance of the patient, and modifies the therapy delivery parameter based on the determined resistance of the patient and the measured electrical parameter value.

34. The external defibrillator of claim 33, wherein the processor controls therapy delivery module to deliver a first defibrillation pulse to the patient according to a value of the therapy delivery parameter prior to modification, controls the measurement module to measure the value of the at least one electrical parameter during delivery of the first defibrillation pulse to the patient, determines the resistance of the patient based on the at least one electrical parameter value, and controls the therapy delivery module to deliver a second defibrillation pulse to the patient according to the modified therapy delivery parameter value.

35. The external defibrillator of claim 21, wherein the circuit includes a receptacle, and the external defibrillator further comprises a plug that is configured for receipt by the receptacle to couple the external defibrillator to the circuit.

* * * * *

UNITED STATES PATENT AND TRADEMARK OFFICE
CERTIFICATE OF CORRECTION

| | | |
|---|---|---|
| PATENT NO. | : 7,725,180 B2 | |
| APPLICATION NO. | : 10/998911 | |
| DATED | : May 25, 2010 | |
| INVENTOR(S) | : Sullivan et al. | |

It is certified that error appears in the above-identified patent and that said Letters Patent is hereby corrected as shown below:

Column 13, Line 29, "$R_{circuit} = (V_{open}\ V_{load}) * R_{load}/V_{load}$"
should read -- $R_{circuit} = (V_{open} - V_{load}) * R_{load}/V_{load}$ --

Column 13, Line 57, "value (126) determines whether determines whether the circuit..."
should read -- value (126) determines whether the circuit... --

Column 16, Line 35, "pulse that the a circuit is capable..."
should read -- pulse that the circuit is capable... --

Signed and Sealed this
Nineteenth Day of July, 2011

David J. Kappos
*Director of the United States Patent and Trademark Office*